(12) United States Patent
Chen et al.

(10) Patent No.: US 8,135,204 B1
(45) Date of Patent: Mar. 13, 2012

(54) COMPUTER-IMPLEMENTED METHODS, CARRIER MEDIA, AND SYSTEMS FOR CREATING A DEFECT SAMPLE FOR USE IN SELECTING ONE OR MORE PARAMETERS OF AN INSPECTION RECIPE

(75) Inventors: Chien-Huei (Adam) Chen, San Jose, CA (US); Barry Becker, San Jose, CA (US); Hong Chen, San Ramon, CA (US); Michael Van Riet, Morgan Hill, CA (US); Chris Maher, Campbell, CA (US); Stephanie Chen, Fremont, CA (US); Suryanarayana Tummala, Tirupathi (IN); Yong Zhang, Cupertino, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 1208 days.

(21) Appl. No.: 11/859,342

(22) Filed: Sep. 21, 2007

(51) Int. Cl.
 *G06K 9/00* (2006.01)
(52) U.S. Cl. .................. 382/141; 356/237.2; 356/237.6; 250/310; 382/145
(58) Field of Classification Search .................. 382/141, 382/145, 149, 151; 356/237.2, 237.4; 702/123, 702/127; 250/310
 See application file for complete search history.

(56) References Cited

U.S. PATENT DOCUMENTS

| 5,991,699 | A | 11/1999 | Kulkarni et al. |
| 6,718,526 | B1 | 4/2004 | Eldredge et al. |
| 6,754,593 | B1* | 6/2004 | Stewart et al. ................... 702/35 |
| 7,440,086 | B2* | 10/2008 | Borowicz et al. ............... 356/72 |
| 2004/0156540 | A1* | 8/2004 | Gao et al. ....................... 382/145 |
| 2006/0082763 | A1* | 4/2006 | Teh et al. ......................... 356/72 |
| 2006/0287751 | A1 | 12/2006 | Dishner et al. |
| 2007/0081151 | A1* | 4/2007 | Shortt et al. ............... 356/237.2 |

* cited by examiner

*Primary Examiner* — Gregory J Toatley
*Assistant Examiner* — Isiaka Akanbi
(74) *Attorney, Agent, or Firm* — Anne Marie Mewherter (57) ABSTRACT

Computer-implemented methods, carrier media, and systems for creating a defect sample for use in selecting one or more parameters of an inspection recipe are provided. One method includes separating defects into bins based on regions in which the defects are located, defect types, and values of the defects for parameter(s) of a detection algorithm. The method also includes determining a number of the defects to be selected from each bin by distributing a user-specified target number of defects across the bins. In addition, the method includes selecting defects from the bins based on the determined numbers thereby creating a defect sample for use in selecting values of parameter(s) of the detection algorithm for use in the inspection recipe.

26 Claims, 1 Drawing Sheet

COMPUTER-IMPLEMENTED METHODS, CARRIER MEDIA, AND SYSTEMS FOR CREATING A DEFECT SAMPLE FOR USE IN SELECTING ONE OR MORE PARAMETERS OF AN INSPECTION RECIPE

BACKGROUND OF THE INVENTION

1. Field of the Invention

This invention generally relates to computer-implemented methods, carrier media, and systems for creating a defect sample for use in selecting one or more parameters of an inspection recipe. Certain embodiments relate to a computer-implemented method for creating a defect sample that has one or more characteristics that are substantially the same as one or more characteristics of all the defects detected on a wafer.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on a specimen such as a reticle and a wafer. Inspection processes have always been an important part of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices. Accordingly, much work in the inspection field has been devoted to designing inspection systems that can detect defects having sizes that were previously negligible.

Many different types of inspection systems have adjustable output acquisition and sensitivity (or defect detection) parameters such that different parameters can be used to detect different defects or avoid sources of unwanted (nuisance) events. Although an inspection system that has adjustable output acquisition and sensitivity parameters presents significant advantages to a semiconductor device manufacturer, these inspection systems are essentially useless if the incorrect output acquisition (e.g., data, signal, and/or image acquisition) and sensitivity parameters are used for an inspection process. For example, incorrect or non-optimized output acquisition parameters may produce such high levels of noise that no defects can be detected in the generated output. In addition, since the defects, process conditions, and noise on a specimen such as a reticle and a wafer may vary dramatically (and since the characteristics of the specimen itself may vary dramatically), the best output acquisition and sensitivity parameters for detecting the defects on a particular specimen may be difficult, if not impossible, to predict. Therefore, although using the correct output acquisition and sensitivity parameters will have a dramatic effect on the results of inspection, it is conceivable that many inspection processes are currently being performed with incorrect or non-optimized output acquisition and sensitivity parameters.

An optimal inspection recipe for a semiconductor layer should detect as many defects of interest (DOI) as possible while maintaining a substantially low nuisance rate. Optimizing an inspection recipe generally involves tuning the parameters used in the recipe until the optimal result is achieved. The set of parameters to be tuned thus depends on the detection algorithm used. In the case of bright field (BF) inspection systems commercially available from KLA-Tencor, San Jose, Calif., the detection algorithms may be either auto-thresholding (AT), segmented auto-thresholding (SAT) or multiple die auto-thresholding (MDAT), and the inspection parameters are segment breaks and thresholds. In the case of dark field (DF) inspection systems commercially available from KLA-Tencor, the detection algorithms may be FAST and HLAT algorithms.

One best known method for recipe optimization is to run a substantially "hot" inspection thereby increasing the likelihood of detecting DOI but at the expense of substantially high nuisance rate. The user then takes this hot lot and the wafer to a scanning electron microscope (SEM) for review. The user reviews the defects using the SEM and classifies the defects as real, nuisance, or DOI. Once enough of each type of defect is classified, the user attempts to set the correct segmentation breaks and threshold values in order to create a recipe that will detect enough of the DOI and have as few as possible of the nuisance defects detected. The more defects that are classified, the better the recipe can be. The user may then re-inspect the wafer using the new recipe and use the SEM to review the defects detected on the wafer using the new recipe. In this manner, the re-inspection and defect review may be performed in an iterative manner until the user determines that satisfactory defect detection can be achieved by the recipe based on defect review results.

One problem with such methods is that it takes significant time to SEM review a single defect. In addition, the need for multiple trips between the inspection system and the SEM adds significant time to the recipe setup. The user would ideally like to review the smallest number of defects possible that would still produce an accurate recipe and be able to do this in one trip to the SEM. However, because of the nature of the distribution of defects in a hot lot, any kind of sampling, including random sampling, that does not take into account the distribution of defects would produce a sampled lot that would be overly weighted towards the nuisance defects, and in most cases, it would not produce a classified lot that was useable for setting segment breakpoints or detection threshold values.

There are many sampling methods used in various technical fields. For semiconductor defect review, the most common method is random sampling of defects based on some selected attributes, e.g., defect size, defect density, or defect clusters. Those methods are designed for statistical process control (SPC). There are some sophisticated methods created for special purposes such as diversity sampling designed for the discovery of defect types. Examples of methods that can be performed for such purposes are described in commonly owned U.S. patent application Ser. No. 11/146,342 by Dishner et al. filed Jun. 6, 2005, which published as U.S. Patent Application Publication No. 2006/0287751 on Dec. 21, 2006, and which is incorporated by reference as if fully set forth herein.

While such sampling methods may be useful for their designed purposes, they are not suitable for recipe optimization. In particular, those sampling methods do not consider the distribution of defects in the space of detection parameters. Furthermore, such methods completely break down when dealing with extremely hot inspection results in which the vast majority of the defects are nuisances. In particular, the randomness of the currently used sampling methods will pick mostly nuisance defects.

Accordingly, it would be advantageous to develop computer-implemented methods, carrier media, and/or systems for efficient sampling of defects for recipe optimization that take into account the distribution of the defects in a typical hot lot to produce a sampled lot that can be taken to a SEM and used to produce a valid set of segment breakpoints and detection thresholds, in a single trip to the SEM.

SUMMARY OF THE INVENTION

The following description of various embodiments of computer-implemented methods, carrier media, and systems is not to be construed in any way as limiting the subject matter of the appended claims.

One embodiment relates to a computer-implemented method for creating a defect sample for use in selecting one or more parameters of an inspection recipe. The method includes separating defects into bins based on regions in which the defects are located, defect type, and values of the defects for one or more parameters of a detection algorithm. The defects are detected on a wafer by performing a hot inspection on the wafer. The detection algorithm is included in an inspection recipe. The method also includes determining a number of the defects to be selected from each bin by distributing a user-specified target number of defects across the bins for different regions and different defect types in proportion to a number of the defects in each of the different regions and having each of the different defect types and across the bins for different values for the one or more parameters. In addition, the method includes selecting defects from the bins based on the determined numbers thereby creating a defect sample for use in selecting values of one or more parameters of the detection algorithm for use in the inspection recipe.

In one embodiment, one or more characteristics of the defect sample are substantially the same as one or more characteristics of the defects detected on the wafer.

In one embodiment, separating the defects includes separating the defects into groups based on the regions and the defect type and separately determining for each group breakpoints defining the values of the defects corresponding to the bins for the different values. In one such embodiment, the breakpoints lie between breakpoints spaced evenly across the values of the defects and breakpoints that result in equal defect populations in the bins for the different values. In another embodiment, separating the defects includes adjusting width of the bins for the different values based on a distribution of the defects across the values of the defects.

In one embodiment, separating the defects includes separating the defects into groups based on the regions and the defect type and separately determining for each group breakpoints defining the values of the defects corresponding to the bins for the different values by generating a histogram for each group and one of the one or more parameters, determining a square root of each of the histograms, and determining the breakpoints such that the bins for the different values of the one of the one or more parameters have substantially equal defect populations in the square root of each of the histograms.

In another embodiment, the one or more parameters of the detection algorithm used to separate the defects include actual detection value. In one such embodiment, separating the defects includes separating the defects into groups based on the regions and the defect type and separately determining for each group breakpoints defining the actual detection values corresponding to the bins for the different values, and the defects having actual detection values below the lowest breakpoint are not separated into the bins.

In one embodiment, the defect type is defined based on polarity. In another embodiment, the one or more parameters of the detection algorithm used to separate the defects include median value and actual detection value.

In one embodiment, distributing the user-specified target number proportionally across the bins for the different regions includes separately determining the number of the defects to be selected from each of the bins for the different regions by dividing a square root of total number of defects in each of the different regions by the square root of the total number of defects detected on the wafer and multiplying results of the dividing by the user-specified target number.

In another embodiment, distributing the user-specified target number proportionally across the bins for the different defect types includes separately determining the number of the defects to be selected from each of the bins for the different defect types in each of the different regions by dividing a square root of number of defects of each of the different defect types in a region by the square root of the total number of defects in the region and multiplying results of the dividing by total number of defects to be selected from the region.

In some embodiments, distributing the user-specified target number across the bins for the different values for the one or more parameters includes substantially evenly distributing the user-specified target number across the bins for the different values.

In one embodiment, separating the defects and determining the numbers cause more of the defects in the defect sample to be selected from a transition area of a threshold curve than a non-transition area of the threshold curve. In another embodiment, at least a majority of the defects detected on the wafer are nuisance defects, and at least a significant number of the defects in the defect sample are not nuisance defects. In an additional embodiment, the defect sample is created without any prior knowledge about the defect type or defect distribution across defect type.

In another embodiment, selecting the defects includes randomly selecting the defects from the bins based on the determined numbers. In one embodiment, selecting the defects includes selecting only one defect from any cluster of defects included in any of the bins. In some embodiments, the one or more parameters of the detection algorithm used to separate the defects include actual detection value, and selecting the defects from the bins includes selecting the defects from the bins in order from the bin corresponding to the highest actual detection value to the bin corresponding to the lowest actual detection value. In a further embodiment, selecting the defects includes selecting the defects from a first bin for the different values, and if the number to be selected from the first bin cannot be selected from the first bin, selecting the defects includes substantially evenly redistributing the number of the defects that cannot be selected from the first bin across other bins for the different values in the same region and defect type as the first bin.

In one embodiment, the inspection recipe includes an inspection recipe for bright field inspection of the wafer. In another embodiment, the inspection recipe includes an inspection recipe for dark field inspection of the wafer.

In one embodiment, separating the defects includes separating the defects into bins based on inspection system channel in which the defects were detected, the regions, the defect type, and the values of the defects for the one or more parameters of the detection algorithm. In one such embodiment, the determining step includes determining the number of the defects to be selected from each bin by further distributing the user-specified target number of defects across the bins for different inspection system channels in proportion to a number of the defects detected by each of the different inspection system channels.

In another embodiment, distributing the user-specified target number of defects across the bins for the different values for the one or more parameters is performed such that a ratio of the numbers of the defects to be selected from different bins for the different values is substantially the same as a ratio of the numbers of the defects in the different bins for the different values.

In one embodiment in which the inspection recipe includes an inspection recipe for dark field inspection of the wafer, separating the defects includes separating the defects into groups based on inspection system channel in which the defects were detected, the regions, and the defect type and separately determining for each group breakpoints defining the values of the defects corresponding to the bins for the different values by generating a cumulated distribute function (CDF) for each group and one of the one or more parameters, determining a square root of each of the cumulated distribute functions, and determining the breakpoints such that the bins for the different values of the one of the one or more parameters have substantially the same values of the cumulated distribute function.

Each of the steps of the method described above may be performed as described further herein. In addition, each of the embodiments of the method described above may include any other step(s) of any other method(s) described herein. Furthermore, each of the embodiments of the method described above may be performed by any of the systems described herein.

Another embodiment relates to a carrier medium that includes program instructions executable on a computer system for performing a computer-implemented method for creating a defect sample for use in selecting one or more parameters of an inspection recipe. The computer-implemented method includes separating defects into bins based on regions in which the defects are located, defect type, and values of the defects for one or more parameters of a detection algorithm. The defects are detected on a wafer by performing a hot inspection on the wafer. The detection algorithm is included in an inspection recipe. The method also includes determining a number of the defects to be selected from each bin by distributing a user-specified target number of defects across the bins for different regions and different defect types in proportion to a number of the defects in each of the different regions and having each of the different defect types and across the bins for different values for the one or more parameters. In addition, the method includes selecting defects from the bins based on the determined numbers thereby creating a defect sample for use in selecting values of one or more parameters of the detection algorithm for use in the inspection recipe.

The carrier medium described above may be further configured as described herein. The steps of the computer-implemented method may be performed as described further herein. In addition, the computer-implemented method for which the program instructions are executable may include any other step(s) of any other method(s) described herein.

An additional embodiment relates to a system configured to create a defect sample for use in selecting one or more parameters of an inspection recipe. The system includes an inspection system configured to detect defects on a wafer by performing a hot inspection on the wafer. The system also includes a computer system configured to separate the defects into bins based on regions in which the defects are located, defect type, and values of the defects for one or more parameters of a detection algorithm. The detection algorithm is included in an inspection recipe. The computer system is also configured to determine a number of the defects to be selected from each bin by distributing a user-specified target number of defects across the bins for different regions and different defect types in proportion to a number of the defects in each of the different regions and having each of the different defect types and across the bins for different values for the one or more parameters. In addition, the computer system is configured to select defects from the bins based on the determined numbers thereby creating a defect sample for use in selecting values of one or more parameters of the detection algorithm for use in the inspection recipe. The system may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

One or more layers may be formed upon a wafer. For example, such layers may include, but are not limited to, a resist, a dielectric material, a conductive material, and a semi-conductive material. Many different types of such layers are known in the art, and the term wafer as used herein is intended to encompass a wafer on which all types of such layers may be formed.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Although embodiments are described herein with respect to wafers, it is to be understood that the embodiments may be used for creating a defect sample for use in selecting one or more parameters of an inspection recipe for inspection of another specimen such as a reticle, which may also be commonly referred to as a mask or a photomask. Many different types of reticles are known in the art, and the terms "reticle," "mask," and "photomask" as used herein are intended to encompass all types of reticles known in the art.

The embodiments described herein generally relate to methods for efficient sampling of defects for recipe optimization purposes. For example, one embodiment relates to a computer-implemented method for creating a defect sample for use in to selecting one or more parameters of an inspection recipe. A "recipe" is generally defined as a set of instructions that can be used by a system such as an inspection system to perform a process such as an inspection process. The methods described herein are not limited in the types of inspection systems for which one or more parameters of an inspection recipe can be selected using a defect sample created as described herein. For example, in one embodiment, the inspection recipe includes an inspection recipe for bright field (BF) inspection of the wafer. In this manner, the inspection system may include a BF inspection system. The BF inspection system may be configured as described further herein. In another embodiment, the inspection recipe includes an inspection recipe for dark field (DF) inspection of the wafer. In this manner, the inspection system may include a DF inspection system. The DF inspection system may have any suitable configuration known in the art. The inspection system may also be configured for BF and DF inspection. In addition, the inspection system may be configured for inspection of patterned wafers and/or unpatterned wafers.

The method includes separating defects into bins based on regions in which the defects are located, defect type, and values of the defects for one or more parameters of a detection algorithm. The defects are detected on a wafer by performing a hot inspection on the wafer. In this manner, the method attempts to produce a sample of the original defect population detected in a hot inspection. A "hot inspection" can be generally defined as an inspection in which a threshold applied to output of a detector of an inspection system is substantially close to the noise floor of the output. The defects may also be detected on more than one wafer by performing hot inspections on the wafers. For example, the defects may be detected on a lot of wafers (i.e., "a hot lot"). In addition, the user may run an inspection resulting in a hot lot.

The embodiments described herein, however, may or may not include performing the hot inspection of the wafer. For example, the embodiments described herein may include acquiring the results of a hot inspection performed on the wafer from an inspection system that performed the hot inspection or from a storage medium (e.g., a storage medium of the inspection system, a fab database, etc.) in which the inspection system stored the results of the hot inspection. In one such example, the features for all of the defects or a user-defined sub-population of the defects may be read by the embodiments described herein (e.g., uploaded from a storage medium or file (such as a KLARF) that includes information about the defects detected by the hot inspection). In any case, the results of the hot inspection may be acquired in any suitable manner (e.g., by scanning the wafer using an inspection system and applying a threshold to output generated by scanning).

In this manner, the method produces a sample of the original defects detected in a hot inspection. The original defects used to produce the sample may also include a subset of the original defects in the hot lot. For example, the user may optionally specify a subset of defects in the lot, provided that the user has a priori knowledge that he/she is not interested in certain types of defects.

The detection algorithm is included in an inspection recipe. The detection algorithm may include any suitable detection algorithm known in the art. In one embodiment, the detection algorithm is an auto-thresholding (AT) algorithm. In an additional embodiment, the detection algorithm is a segmented auto-thresholding (SAT) detection algorithm. In another embodiment, the detection algorithm is a multiple die auto-thresholding (MDAT) detection algorithm. Such detection algorithms may be particularly suitable for BF inspection. However, the detection algorithm may include a detection algorithm that is particularly suitable for DF inspection. For example, in one embodiment, the detection algorithm includes a FAST algorithm or a HLAT algorithm. The detection algorithm preferably includes the detection algorithm for which one or more parameters will be selected using the created defect sample.

The regions used to separate the defects may be defined in any suitable manner (e.g., different regions may correspond to different portions of a design printed (or to be printed) on the wafer), and the defects may be separated based on region using any suitable method, algorithm, system, or technique. In one embodiment, the defect type is defined based on polarity. For example, the method may include dividing all of the defects into regions and types based on polarity. Polarity can be generally defined as a measure of whether a defect appears bright or dark with respect to the background surrounding the defect. Different types of defects appear bright and dark with respect to the background. Therefore, the defects may be separated into different types based on polarity. The defects may be separated into defect types based on polarity using any suitable method, algorithm, system, or technique. In addition, although defining defect types based on polarity may provide sufficient separation between defect types, the defect types may be based on one or more other characteristics of the defects that can be determined from output of a detector of an inspection system and/or inspection results.

Separating the defects into bins may also be performed based on any other information about the defects that is available or can be determined before the separating step is performed. For example, in some embodiments, separating the defects includes separating the defects into bins based on inspection system channel in which the defects were detected, the regions, the defect type, and the values of the defects for the one or more parameters of the detection algorithm. In this manner, if the defects are detected by an inspection system that includes more than one channel (e.g., more than one detection channel (or detector) that generates output for the wafer during the hot inspection), then the defects detected on the wafer may be separated such that defects detected by different channels are separated into different bins. In addition, the defects may be separated into bins based on inspection system channel, then based on region, and finally based on defect type. Separating the defects in this manner may be advantageous since different channels may detect different types of defects of interest (DOI), DOI at different capture rates, nuisance at different suppression rates, etc. thereby potentially allowing for better separation between DOI and nuisance prior to sampling and therefore better sampling of the defects.

Once the defects have been separated into regions and types (and possibly inspection system channels) as described above, each group may then be processed individually. For example, in one embodiment, separating the defects includes separating the defects into groups based on the regions and the defect type (and possibly inspection system channel) and separately determining for each group breakpoints (i.e., thresholds or cutlines) defining the values of the defects corresponding to the bins for the different values. The defects in each region/type (and possibly inspection system channel) group may then be further divided into smaller groups based on the determined breakpoints.

In some embodiments, the one or more parameters of the detection algorithm used to separate the defects include median value and actual detection value. In this manner, the processing that is performed on each group includes defining a set of breakpoints to be used for the values of the defects (e.g., median value and the actual detection value). However, the one or more parameters of the detection algorithm used to separate the defects may include any suitable parameters of any suitable detection algorithm and may, therefore, vary depending on the detection algorithm included in the inspection recipe. For example, as described above, the one or more parameters may include median value and/or actual detection value included in a detection algorithm such as AT, SAT, and MDAT. In another example, the one or more parameters may include algorithm-related features of the defects such as defect difference intensity, FAST algorithm threshold, HLAT algorithm threshold, polarity, noise, absolute minimum (ABSMIN), or some combination thereof. Such parameters may be included in a detection algorithm used for DF inspection.

In one embodiment, the breakpoints lie between breakpoints spaced evenly across the values of the defects and breakpoints that result in equal defect populations in the bins for the different values. For example, the breakpoints described above are preferably determined in such a way that they reside somewhere between those that would be obtained by defining the breakpoints as equidistant breakpoints and breakpoints that would result in equal population bins. Such breakpoints may be determined according to any embodiments described herein.

In some embodiments, separating the defects includes adjusting width of the bins for the different values based on a distribution of the defects across the values of the defects. In this manner, the method may include adjusting bin width based on the distribution of the defects. For example, in one embodiment, separating the defects includes separating the defects into groups based on the regions and the defect type (and possibly inspection system channel), which may be performed as described above, and separately determining for each group breakpoints defining the values of the defects corresponding to the bins for the different values by generating a histogram for each group and one of the one or more parameters, determining a square root of each of the histograms, and determining the breakpoints such that the bins for the different values of the one of the one or more parameters have substantially equal defect populations in the square root of each of the histograms. In one such example, the defects may be binned into separate histograms for each region and type (e.g., bright or dark) based on their median values. In a similar manner, the defects may be binned into separate histograms for each channel, region, and polarity (e.g., bright or dark). The square root for each histogram may then be calculated. Breakpoints may then be set such that the bins for different ranges of the values (e.g., the median values) have equal populations in the square root histograms. The defects may then be re-segmented based on these bins.

In one embodiment in which the inspection recipe includes an inspection recipe for DF inspection of the wafer, separating the defects includes separating the defects into groups based on inspection system channel in which the defects were detected, the regions, and the defect type and separately determining for each group breakpoints defining the values of the defects corresponding to the bins for the different values by generating a cumulated distribute function (CDF) for each group and one of the one or more parameters, determining a square root of each of the CDFs, and determining the breakpoints such that the bins for the different values of the one or more one or more parameters have substantially the same values of the CDF. Therefore, separating the defects may be performed as described above, but in the DF case, a CDF may be used instead of a histogram. In addition, in the DF case, instead of determining the breakpoints such that the bins for the different values have substantially equal defect populations in the square root of each of the histograms, the breakpoints may be determined such that the bins for the different values have substantially the same CDF value. The CDF may include any suitable CDF known in the art and may be generated in any suitable manner known in the art.

In another embodiment, the one or more parameters of the detection algorithm used to separate the defects include actual detection value, and separating the defects includes separating the defects into groups based on the regions and the defect type and separately determining for each group breakpoints defining the actual detection values corresponding to the bins for the different values. For example, the defects that were re-segmented as described above may be binned into separate histograms for each region, type, and range of median values determined above, based on their actual detection values. Breakpoints may then be calculated for the actual detection values in a similar manner to that described above. In a similar manner, the defects may be binned into separate histograms for each inspection system channel, region, type, and range of first values for a parameter of the detection algorithm based on their second values for another parameter of the detection algorithm. Breakpoints may then be calculated for the second values in a similar manner to that described above.

In one such embodiment, the defects having actual detection values below the lowest breakpoint for the actual detection values are not separated into the bins. For example, unlike breakpoints determined for the median values, there may be a limit that is applied to the actual detection values. The limit may be the lowest breakpoint for the actual detection values, below which all defects are ignored (e.g., since most of the defects below the lowest breakpoint for the actual detection values can be assumed to be nuisance defects). This limit may be determined by taking the first derivative of the square root of each square root histogram and searching for the rightmost value that is below a certain value or if that point is not found then the most negative position may be used. In addition, the method of determining the lowest actual detection value to be considered by the embodiments described herein can be modified to derive the lowest actual detection value from the existing data instead of using a fixed threshold value. In this manner, the lowest actual detection value of defects to be considered in the embodiments described herein may be adaptive or set. Limits may be applied in a similar manner to any other parameters of detection algorithms described herein.

A 4-dimensional (4D) array or n-dimensional array of bins may, therefore, be defined. The basis axes in the 4D space may be the region ID, defect type, re-segmented median value, and actual detection value bin. The basis axes in the n-dimensional space may be the inspection system channel, region ID, defect type, and value(s) for one or more parameters of the detection algorithm. Each defect is then assigned to one bin. If a defect could possibly be assigned to more than one bin, it is only assigned to the bin in which the defect is maximally defective. In this manner, the method may include separating the defects into bins in 4D space or n-dimensional space. In addition, the method may include binning the defects into a 4D histogram based on the defects' region type, polarity, median value, and actual detection value. In a similar manner, the method may include binning the defects into an n-dimensional histogram based on the inspection system channel, region type, polarity, and value(s) of one or more parameters of the detection algorithm. For example, the method may include separating the defects into bins based on the inspection system channel, region, defect type, and value(s) of one or more of the following parameters of detection algorithms: defect difference intensity, FAST algorithm threshold, HLAT algorithm threshold, polarity, noise, ABSMIN, or some combination thereof. In this manner, the methods described herein may form n-dimensional feature space using one or more of the above algorithm-related features for better recipe tuning. Using channels and n-dimensional space may be particularly advantageous for creating defect samples for use in selecting one or more parameters of DF inspection recipes.

The user may specify a target number of defects to be sampled. Once the user specifies the target number, the user may run an algorithm configured to perform one or more embodiments described herein to create a defect sample that includes a number of defects that is close to (but perhaps not exactly) the number that was specified. For example, the method includes determining a number of the defects to be selected from each bin by distributing a user-specified target number of defects across the bins for different regions and different defect types in proportion to a number of the defects in each of the different regions and having each of the different defect types and across the bins for different values for the one or more parameters. In this manner, the method may include weighted distribution of bin counts. In addition, in one embodiment, distributing the user-specified target number across the bins for the different values for the one or more parameters includes substantially evenly distributing the user-specified target number across the bins for the different values. For example, once the defects have been divided into their appropriate bins across region, type, median value, and actual detection value, the user-specified target number of defects may be distributed across, first all of the regions based on the proportion of all defects in each region, then within a region based on the proportion of all defects of each type of defect, and then finally substantially evenly across the median value (segment) and actual detection value bins. In this manner, the method may include calculating the target number for sampling in each bin of a 4D histogram.

In one embodiment, the determining step includes determining the number of the defects to be selected from each bin by further distributing the user-specified target number of defects across the bins for different inspection system channels in proportion to a number of the defects detected by each of the different inspection system channels. In this manner, the user-specified target number of defects can be distributed proportionally across inspection system channel, region, and defect type. As such, the method may use a weighted sampling strategy to generate sampled defects.

In addition, in some embodiments, distributing the user-specified target number of defects across the bins for the different values for the one or more parameters is performed such that a ratio of the numbers of the defects to be selected from different bins for the different values is substantially the same as a ratio of the numbers of the defects in the different bins for the different values. In this manner, instead of distributing the user-specified target number substantially evenly across the bins for the different values, the user-specified target number may be distributed based on the relative number of defects in different bins for different values of the one or more parameters of the detection algorithm.

In one embodiment, distributing the user-specified target number proportionally across the bins for the different regions includes separately determining the number of the defects to be selected from each of the bins for the different regions by dividing a square root of total number of defects in each of the different regions by the square root of the total number of defects detected on the wafer and multiplying results of the dividing by the user-specified target number. For example, all of the defects in each region may be counted, and the ratio of the square root of each total can then be used to distribute the target number of defects to be sampled across region. Adjusting the bin counts of the regions by the square root is advantageous to minimize the influence of high density bins on the defect sample (particularly since high density bins tend to correspond to nuisance defect bins).

In another embodiment, distributing the user-specified target number proportionally across the bins for the different defect types includes separately determining the number of the defects to be selected from each of the bins for the different defect types in each of the different regions by dividing a square root of number of defects of each of the different defect types in a region by the square root of the total number of defects in the region and multiplying results of the dividing by total number of defects to be selected from the region. For example, the process described above for distributing the target number of defects to be sampled across region may be performed again, but this time working with each region individually the defects of each type are counted and again the target population for that region is distributed across all of the defect type bins in that region based on the proportion of the square root of each defect type's count. Adjusting the bin counts of the defect types in each region by the square root is advantageous as described further above.

In a similar manner, in one embodiment, distributing the user-specified target number proportionally across the bins for the different inspection system channels includes separately determining the number of the defects to be selected from each of the bins for the different inspection system channels by dividing a square root of total number of defects detected by each of the different inspection system channels by the square root of the total number of defects detected on the wafer by all of the different inspection system channels and multiplying results of the dividing by the user-specified target number. For example, all of the defects detected by each inspection system channel may be counted, and the ratio of the square root of each total can then be used to distribute the target number of defects to be sampled across inspection system channel. Adjusting the bin counts of the channels by the square root is advantageous to minimize the influence of high density bins on the defect sample (particularly since high density bins tend to correspond to nuisance defect bins). Distributing the user-specified target number of defects across the bins for different inspection system channels may be performed before the user-specified target number of defects is distributed across region and type, which may be performed as described above. For examples, after distributing the user-specified target number across inspection system channel, the user-specified target number may be distributed across region as described above but using the total number of defects detected by an inspection system channel in place of total number of defects detected on the wafer for the regions corresponding to that channel.

The target number of defects for each region and type may then be substantially evenly distributed across all of the bins for the different values with that region and type. In other words, the target number of defects for each region and type may be distributed such that the target numbers for all of the bins for the different values with that region and type are substantially the same.

Alternatively, the target number of defects for each inspection system channel, region, and type may be distributed across the bins for the different values with that channel, region, and type based on the ratio of the numbers of defects in different bins for different values such that a ratio of the numbers of the defects to be selected from different bins for the different values is substantially the same as a ratio of the numbers of the defects in the different bins for the different regions. In this manner, the target number of defects for each channel, region, and defect type may be distributed with the same defect ratio across all of the bins for that channel, region, and defect type. For example, there may be 100 defects in bin 1, and 50 defects in bin 2. Therefore, the number of defects to be selected from bin 1 determined as described above may be 2, and the number of defects to be selected from bin 2 determined as described above may be 1. Distributing the user-specified target number across the bins for the different values in this manner will guarantee that a histogram for the sampled defects (i.e., the output defect histogram) will have substantially the same shape as a histogram for the defects detected on the wafer (i.e., the original defect histogram).

The embodiments described herein for determining breakpoint placement for both median values and actual detection values along with distributing the target number of defects across the different regions and types were constructed to work with a representative sample of lots that were both regular inspection and one step threshold setup (OSTS) lots. If additional types of distributions are observed in the defects detected on the wafer, then the methods described herein used to set these breakpoints and distribute the target number of defects could be modified to use different equalization methods such as, but not limited to, switching from using the square root operation to using a higher order root (e.g., a cube root), a logarithmic function, or any other function that will "smooth out" differences between high defect counts and low defect counts across a dimension used for binning.

The method further includes selecting defects from the bins based on the determined numbers thereby creating a defect sample for use in selecting values of one or more parameters of the detection algorithm for use in the inspection recipe. For example, in one embodiment, selecting the defects includes randomly selecting the defects from the bins based on the determined numbers. In one such example, at the point at which the numbers have been determined as described above, a random sample of the distributed target is taken from each bin, and these defects constitute the sampled defects.

In one embodiment, selecting the defects includes selecting only one defect from any cluster of defects included in any of the bins. For example, if a defect is included in a cluster from which another defect has already been sampled, then it will not be sampled. In this manner, clustered defects may be excluded from sampling such that any given cluster is not sampled more than once. Defects may be clustered such that defects having spatial relationships with one another (e.g., defects that are relatively close together or collectively exhibit a characteristic defect signature such as that of a scratch) are considered to be a single defect event. For example, the detection algorithm may detect a number of individual defects on the wafer that are actually part of a single defect event (e.g., light point defects that collectively represent a scratch). Spatial signature analysis may be used to identify spatial correlation among a group of defects that indicates a common defect causality. Clustering of defects may be performed in any suitable manner. For example, defect clustering may be performed as described in commonly owned U.S. Pat. Nos. 5,991,699 to Kulkami et al. and 6,718,526 to Eldredge et al., which are incorporated by reference as if fully set forth herein. The embodiments described herein may include any step(s) of any method(s) described in these patents. Therefore, since a cluster of individual defects may signify, a single defect event, sampling only one of the individual defects from any cluster may be advantageous (e.g., to avoid weighting the defect sample to a particular defect or defect type and since sampling of one defect of any cluster will usually be sufficient to provide information about the defect cluster for selection of the one or more parameters of the inspection recipe). In this manner, each defect event may be sampled only once by the embodiments described herein.

In another embodiment, the one or more parameters of the detection algorithm used to separate the defects include actual detection value, and selecting the defects from the bins includes selecting the defects from the bins in order from the bin corresponding to the highest actual detection value to the bin corresponding to the lowest actual detection value. For example, for a given region, type, and range of median values, selection may start with the highest actual detection value bin by attempting to randomly select the target number of defects from that bin. Such embodiments may be advantageous in that defects that exhibit relatively high actual detection values tend to be real defects as opposed to nuisance defects. Therefore, attempting to sample the target number of defects from the highest actual detection value bin before other bins and before redistribution of the target numbers as described further herein may be advantageous to maximize the number of real defects, and therefore potential DOI, included in the sample. In addition, attempting to sample the target number of defects from the bins in order from the highest actual detection value bin to the lowest actual detection value bin may be advantageous since the highest actual detection value bin will most likely contain the fewest defects of the bins thereby allowing sampling to be performed in order from the least populated bins to the most populated bins thereby making any redistribution of the target numbers as described further herein easier and more effective. Selecting the defects from bins for other parameter(s) of another detection algorithm may be performed in an order corresponding to a similar or different trend in values of DOI and/or nuisance for the other parameter(s).

In an additional embodiment, selecting the defects includes selecting the defects from a first bin for the different values, and if the number to be selected from the first bin cannot be selected from the first bin, selecting the defects includes substantially evenly redistributing the number of the defects that cannot be selected from the first bin across other bins for the different values in the same region and defect type (and possibly inspection system channel) as the first bin. For example, it may not be possible to select the target number of defects from a bin if the number of defect clusters plus the number of non-clustered individual defects in the bin is less than the target number. If the target number of defects for a bin (e.g., the bin corresponding to the highest actual detection values in a region, defect type, and median value range) was not sampled from the bin, then the remaining bin target to be sampled may be substantially evenly redistributed across the remaining bins with the same region, defect type, and median value range. This process may be repeated until all bins with a given region, defect type, and median value range have been sampled. Again, any defect that is in a cluster from which a defect has already been sampled will be ignored (not sampled). In this manner, the method may include reassigning the sampling quota to more populated bins.

In a similar manner, if after sampling all bins within a given region, defect type, and median value range, the target number of defects was not sampled, then the remaining target may be redistributed evenly amongst the remaining bins for other ranges of median values in the given region and defect type. Again, any defect that belongs to a cluster from which a defect has already been sampled will be ignored. If after sampling defects from all bins in a given region and defect type, the target number was not reached for the defect type, then the remaining defect type target will be distributed across other defect types in the given region in the same manner that the original target was distributed except that the already sampled defect types are ignored. Again, any defect that belongs to a cluster from which a defect has already been sampled will be ignored. If after sampling defects from all bins in a given region, the region target number has not been reached for that region, then the remaining region target may be redistributed across the remaining bins in the manner that the original total was distributed, ignoring any already sampled regions. Again, any defect that belongs to a cluster from which a defect has already been sampled will be ignored.

In a similar manner, if after selecting defects from all bins for an inspection system channel, the inspection system channel target number has not been reached for that channel, then the remaining channel target may be redistributed across the remaining bins in the manner that the original total was distributed, ignoring any already sampled channels. In addition, the redistribution described above may be performed regardless of the dimensions used to separate the defects into the bins. In other words, the redistribution of the target numbers described above can be performed across all dimensions of the bins from which the defects are sampled.

If after sampling all regions (or channels) the total target has not been met, the process of sampling may be repeated starting with distributing the target number of defects to be sampled across each region (or each channel), using just the remaining target number of defects, instead of the original target. Again, any defect that belongs to a cluster from which a defect has already been sampled will be ignored. In a similar manner, the method may include reassigning un-fulfilled target numbers to the sampling of the next dimension (e.g., if the target number of defects cannot be selected from the actual detection value bins in a median value bin, the remaining target number of defects may be distributed across bins for other median values in a manner similar to that described above). These steps may be repeated until the original target is reached or until no new defects were sampled in a given repeat.

The method embodiments described herein may, therefore, be "smart" sampling methods. For example, in one embodiment, at least a majority of the defects detected on the wafer are nuisance defects, and at least a significant number of the defects in the defect sample are not nuisance defects. In particular, the embodiments, described herein may advantageously be used to create a defect sample using defects detected in a hot inspection, which will include a substantial number of nuisance defects due to the nature of hot inspections. However, due to the manner in which the defects are separated as described herein and the manner in which the target number of defects is distributed across bins as described herein, the created defect sample will include a substantial number of DOI (i.e., not nuisance defects). Therefore, the embodiments described herein allow a hot inspection to be performed to catch as many DOI as possible while preventing the substantial nuisance defect detection associated with hot inspections from interfering with the creation of a suitable defect sample for recipe setup and/or optimization.

In one embodiment, separating the defects and determining the numbers cause more of the defects in the defect sample to be selected from a transition area of a threshold curve than a non-transition area of the threshold curve. The transition area of the threshold curve may be the area in which optimum thresholds may be more likely to be located and/or the area from which one or more thresholds may more likely be selected. Selecting the defects as described herein may include sampling more of the defects falling in the transition area of the threshold curve. For example, the embodiments described herein effectively concentrate sampling from areas in which viable thresholds for a defect detection algorithm might be while also sampling sufficiently from other areas. The areas of the threshold curve in which viable thresholds may be located may be determined based on a priori knowledge about thresholds that may be suitable or based on the general shape of the curve (e.g., in a reverse cumulative histogram, the transition area of the threshold curve may include the "tail" above the peak, which is located at lower values in the reverse cumulative histogram). However, the embodiments described herein can create a defect sample that includes more defects in the transition area of the threshold curve than the non-transition area without such a priori knowledge. For instance, the embodiments described herein may distribute the number of defects to be selected across the bins in a manner that weights the target number away from bins with significant numbers of defects having relatively low values for the parameters of the detection algorithm and toward bins with lower numbers of defects having higher values for the parameters of the detection algorithm. Therefore, the embodiments described herein distribute the number of defects to be selected across the bins in a manner that weights the target number away from bins that likely include a substantial number of nuisance defects and toward bins that likely include a substantial number of DOI.

In one embodiment, one or more characteristics of the defect sample are substantially the same as one or more characteristics of the defects detected on the wafer. In particular, the defect sample may have one or more characteristics that are substantially the same as one or more characteristics of all of the defects detected on the wafer. For example, the sample of defects may have similar operating curves as the original defect population. In particular, the sample created as described herein will tend to have the same shape of operating curve as the original defect population in a sensitivity tuner. For example, if a value of a parameter of the defect detection algorithm is plotted as a function of defect count for an entire defect population (e.g., in a reverse cumulative histogram) and for the corresponding defect sample created as described herein, the curve in both plots will have substantially the same characteristics (e.g., shape). Plots generated for the entire defect population and the created defect sample in multidimensional space will also exhibit substantially the same characteristics (e.g., shape). Therefore, the embodiments described herein can advantageously be used to create a defect sample that substantially accurately represents the entire population of defects while not being overwhelmed by nuisance defects.

In another embodiment, the defect sample is created without any prior knowledge about the defect type or defect distribution across defect type. For example, one advantage of the embodiments described herein is that without any a priori knowledge of the defect type or their distribution the user can get a sample of defects from a defect population from a hot inspection.

Defect samples created as described herein may be used for selecting one or more parameters of an inspection recipe in a number of different manners. For example, the user may use a defect review system such as a scanning electron microscope (SEM) to classify the defects in the defect sample. The user may then use the classified defects to setup a recipe. In addition, as described above, the defect samples created as described herein will tend to produce the same shape of operating curves as the original defect populations. As such, by making a single trip to the SEM or other defect review system to classify the sampled defects, the user is likely to be able to create a valid recipe thereby eliminating the many trips back and forth between the inspection system and the defect review system necessary in other inspection recipe setup and optimization methods thereby reducing the time needed to produce an acceptable recipe. In addition, the defect samples created as described herein provide great value in terms of setting up recipes quickly and achieving higher sensitivity.

Defect samples created according to embodiments described herein may also be used to optimize an inspection recipe (e.g., optimize one or more parameters of a detection algorithm included in an inspection recipe). In addition, defect samples created as described herein may be used to optimize any type of inspection recipe (e.g., a DF inspection recipe or a BF inspection recipe) that includes any type of detection algorithm (e.g., a FAST algorithm, an HLAT algorithm, an AT algorithm, a SAT algorithm, a MDAT algorithm, etc.).

Furthermore, although embodiments described herein can be used to select one or more parameters of a detection algorithm that was used to detect the defects on the wafer, the defect samples created as described herein may be used to select any other parameters of an inspection recipe. For example, the defect samples created as described herein may be used to create an entirely new inspection recipe. In addition, the defect samples may be used to select a different inspection recipe or a different detection algorithm for use in an inspection recipe for the wafers. The defect samples created as described herein may also be used to select one or more optical parameters of an inspection system for use in an inspection recipe. The one or more optical parameters of the inspection system that may be selected using the defect samples created as described herein may include any adjustable optical parameters of the inspection system (e.g., wavelength of illumination, polarization of illumination, angle of incidence, angle of collection, polarization of collection, etc.).

Each of the embodiments of the method described above may include any other step(s) of any other method(s) described herein. Furthermore, each of the embodiments of the method described above may be performed by any of the systems described herein.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after the method selects the defects, the method may include storing the created defect sample in a storage medium. Storing the created defect sample may include storing any information about the created defect sample that the user can access and use to review the defects on a defect review tool (e.g., a SEM) in order to classify the defects and determine one or more appropriate parameters for the detection algorithm for the inspection recipe. Furthermore, the results may be stored "permanently," "semi-permanently," temporarily, or for some period of time. For example, the storage medium may be random access memory (RAM), and the results may not necessarily persist indefinitely in the storage medium.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 1:
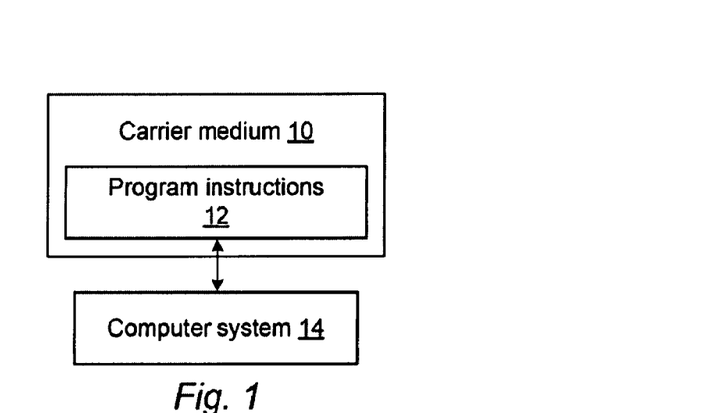
FIG. 1 is a block diagram illustrating one embodiment of a carrier medium that includes program instructions executable on a computer system for performing one or more of the computer-implemented methods described herein.

An additional embodiment relates to a carrier medium that includes program instructions executable on a computer system for performing a computer-implemented method for creating a defect sample for use in selecting one or more parameters of an inspection recipe. One such embodiment is shown in FIG. 1. In particular, as shown in FIG. 1, carrier medium 10 includes program instructions 12 executable on computer system 14.

The computer-implemented method includes separating defects into bins based on regions in which the defects are located, defect type, and values of the defects for one or more parameters of a detection algorithm. Separating the defects may be performed according to any of the embodiments described herein. The defects are detected on a wafer by performing a hot inspection on the wafer. The hot inspection of the wafer may be performed according to any of the embodiments described herein. The detection algorithm is included in an inspection recipe. The detection algorithm may include any of the detection algorithms described herein or any other suitable detection algorithm.

The method also includes determining a number of the defects to be selected from each bin by distributing a user-specified target number of the defects across the bins for different regions and different defect types in proportion to a number of the defects in each of the different regions and having each of the different defect types and across the bins for the different values for the one or more parameters. Determining the numbers may be performed according to any of the embodiments described herein.

In addition, the method includes selecting defects from the bins based on the determined numbers thereby creating a defect sample for use in selecting values of one or more parameters of the detection algorithm for use in the inspection recipe. Selecting the defects may be performed according to any of the embodiments described further herein. The one or more parameters for which values are selected may include, of the parameter(s) described herein. The computer-implemented method for which the program instructions are executable may include any other step(s) described herein.

Program instructions 12 implementing methods such as those described herein may be transmitted over or stored on carrier medium 10. The carrier medium may be a transmission medium such as a wire, cable, or wireless transmission link. The carrier medium may also be a storage medium such as a read-only memory, a random access memory, a magnetic or optical disk, or a magnetic tape.

The program instructions may be implemented in any of various ways, including procedure-based techniques, component-based techniques, and/or object-oriented techniques, among others. For example, the program instructions may be implemented using ActiveX controls, C++ objects, JavaBeans, Matlab, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 2:
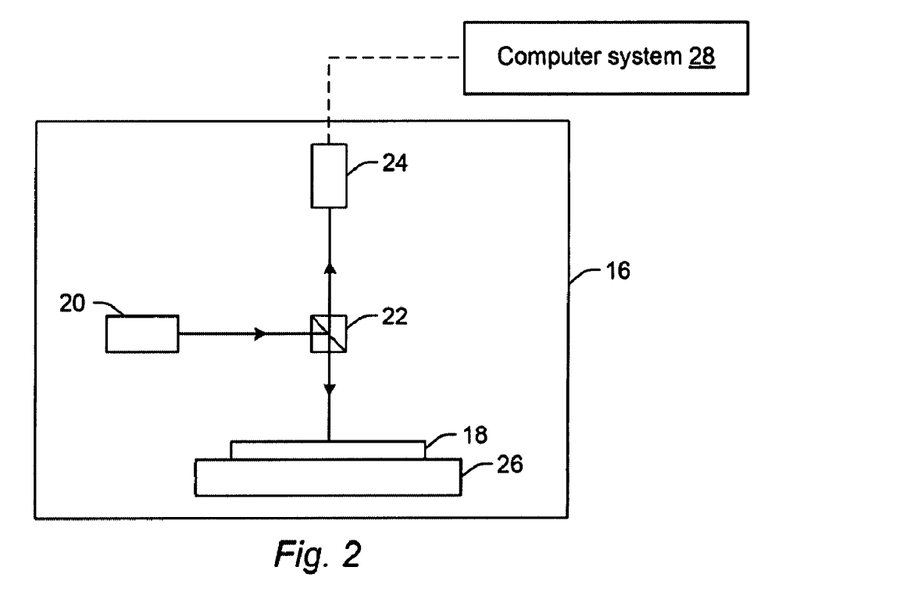
FIG. 2 is a schematic diagram illustrating a side view of one embodiment of a system configured to create a defect sample for use in selecting one or more parameters of an inspection recipe.

Another embodiment relates to a system configured to create a defect sample for use in selecting one or more parameters of an inspection recipe. The system includes an inspection system configured to detect defects on a wafer by performing a hot inspection on the wafer. One embodiment of such a system is shown in FIG. 2. For example, as shown in FIG. 2, the system includes inspection system 16. Inspection system 16 is configured to detect defects on wafer 18.

In one embodiment, inspection system 16 includes light source 20. Light source 20 may include any appropriate light source known in the art. Light source 20 may be configured to direct light to beam splitter 22. Beam splitter 22 may be configured to direct light from light source 20 to wafer 18 at a substantially normal angle of incidence. Beam splitter 22 may include any appropriate optical component known in the art.

Light reflected from wafer 18 may pass through beam splitter 22 to detector 24. Detector 24 may include any appropriate detector known in the art. Output generated by detector 24 may be used to detect defects on wafer 18. For example, computer system 28 may be configured to detect defects on wafer 18 using output generated by the detector. The computer system may use any method and/or algorithm known in the art to detect defects on the wafer. In addition, the computer system may preferably use a detection algorithm, which is included in an inspection recipe for which one or more parameters will be selected using the created defect sample, to detect the defects on the wafer. Parameters of the detection algorithm used to detect the defects on the wafer may be parameters suitable for hot inspection of the wafer (e.g., a threshold that is substantially close to the noise floor of the output generated by the detector). Hot inspection of the wafer may be further performed as described herein. The computer system may be coupled to the detector in any suitable manner (e.g., by one or more transmission media indicated by the dotted line shown in FIG. 2, which may include any suitable transmission media known in the art) such that the computer system can receive the output generated by the detector. Furthermore, if the inspection system includes more than one detector (not shown), the computer system may be coupled to each detector as described above. Computer system 28 may be further configured as described herein. During inspection, wafer 18 may be disposed on stage 26. Stage 26 may include any appropriate mechanical and/or robotic assembly known in the art. The inspection system shown in FIG. 2 may also include any other suitable components (not shown) known in the art.

As shown in FIG. 2, the inspection system is configured to detect light specularly reflected from the wafer. In this manner, the inspection system shown in FIG. 2 is configured as a BF inspection system. However, the inspection system may be replaced by an inspection system configured as a DF inspection system, an edge contrast (EC) inspection system, an aperture mode inspection system, or any other optical inspection system known in the art. In addition, the inspection system may be configured to perform one or more inspection modes. For example, the inspection system shown in FIG. 2 may be configured to perform DF inspection by altering an angle of incidence at which the light is directed to the wafer and/or an angle at which light is collected from the wafer. In another example, the inspection system shown in FIG. 2 may be configured such that one or more optical components (not shown) such as apertures may be positioned in the illumination path and the collection path such that the inspection system can perform EC mode inspection and/or an aperture mode of inspection.

It is noted that FIG. 2 is provided herein to generally illustrate one configuration of an inspection system that may be included in the system embodiments described herein. Obviously, the inspection system configuration described herein may be altered to optimize the performance of the inspection system as is normally performed when designing a commercial inspection system. In addition, the systems described herein may be implemented using an existing inspection system (e.g., by adding functionality described herein to an existing inspection system) such as the 236x and 28xx series of tools and the Puma 9000 and 9100 series of tools that are commercially available from KLA-Tencor, San Jose, Calif. For some such systems, the methods described herein may be provided as optional functionality of the system (e.g., in addition to other functionality of the system). Alternatively, the system described herein may be designed "from scratch" to provide a completely new system.

In another embodiment, the optical inspection system shown in FIG. 2 may be replaced by an electron beam inspection system. Examples of commercially available electron beam inspection systems that may be included in the system of FIG. 2 include the eS25, eS30, and eS31 systems from KLA-Tencor.

Computer system 28 may be configured to perform one or more of the computer-implemented method embodiments described herein (e.g., based on defects detected by the computer system). For example, the computer system is configured to separate the defects into bins based on regions in which the defects are located, defect type, and values of the defects for one or more parameters of a detection algorithm. The detection algorithm is included in an inspection recipe. The detection algorithm may include any of the detection algorithms described herein. The computer system may be configured to separate the defects according to any of the embodiments described herein. The computer system is also configured to determine a number of the defects to be selected from each bin by distributing a user-specified target number of defects across the bins for different regions and different defect types in proportion to a number of the defects in each of the different regions and having each of the different defect types and across the bins for different values for the one or more parameters. The computer system may be configured to determine the numbers according to any embodiments described herein. In addition, the computer system is configured to select defects from the bins based on the determined numbers thereby creating a defect sample for use in selecting values of one or more parameters of the detection algorithm for use in the inspection recipe. The computer system may be configured to select the defects according to any of the embodiments described herein. The one or more parameters for which values are selected may include any of the parameter(s) described herein.

In embodiments of the system that include the inspection system, computer system 28 may be coupled to the inspection system as described further herein. Computer system 28 described above may alternatively be configured as a stand-alone system that does not form part of a process, inspection, metrology, review, or other tool. In such an embodiment, computer system 28 may be configured to receive and/or acquire data or information from other systems (e.g., inspection results from an inspection system) by a transmission medium that may include "wired" and/or "wireless" portions. In this manner, the transmission medium may serve as a data link between the computer system and the other system. In addition, computer system 28 may send data to another system via the transmission medium. Such data may include, for example, information about the defect sample created by the computer system. Alternatively, computer system 28 may form part of the inspection system or part of a defect review system (not shown).

The embodiments of the system shown in FIG. 2 may be further configured as described herein. In addition, the system may be configured to perform any step(s) of any of the method embodiment(s) described herein.

Further modifications and alternative embodiments of various aspects of the invention may be apparent to those skilled in the art in view of this description. For example, computer-implemented methods, carrier media, and systems for creating a defect sample for use in selecting one or more parameters of an inspection recipe are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for creating a defect sample for use in selecting one or more parameters of an inspection recipe, comprising:

separating defects into bins based on regions in which the defects are located, defect type, and values of the defects for one or more parameters of a detection algorithm, wherein the defects are detected on a wafer by performing a hot inspection on the wafer, and wherein the detection algorithm is included in an inspection recipe;

determining a number of the defects to be selected from each bin by distributing a user-specified target number of defects across the bins for different regions and different defect types in proportion to a number of the defects in each of the different regions and having each of the different defect types and across the bins for different values for the one or more parameters, wherein distributing the user-specified target number proportionally across the bins for the different regions comprises separately determining the number of the defects to be selected from each of the bins for the different regions by dividing a square root of total number of defects in each of the different regions by the square root of the total number of defects detected on the wafer and multiplying results of said dividing by the user-specified target number; and selecting defects from the bins based on the determined numbers thereby creating a defect sample for use in selecting values of one or more parameters of the detection algorithm for use in the inspection recipe.

2. The method of claim 1, wherein one or more characteristics of the defect sample are substantially the same as one or more characteristics of the defects detected on the wafer.

3. The method of claim 1, wherein said separating comprises separating the defects into groups based on the regions and the defect type and separately determining for each group breakpoints defining the values of the defects corresponding to the bins for the different values.

4. The method of claim 1, wherein said separating comprises separating the defects into groups based on the regions and the defect type and separately determining for each group breakpoints defining the values of the defects corresponding to the bins for the different values, and wherein the breakpoints lie between breakpoints spaced evenly across the values of the defects and breakpoints that result in equal defect populations in the bins for the different values.

5. The method of claim 1, wherein said separating comprises adjusting width of the bins for the different values based on a distribution of the defects across the values of the defects.

6. The method of claim 1, wherein said separating comprises separating the defects into groups based on the regions and the defect type and separately determining for each group breakpoints defining the values of the defects corresponding to the bins for the different values by generating a histogram for each group and one of the one or more parameters, determining a square root of each of the histograms, and determining the breakpoints such that the bins for the different values of the one of the one or more parameters have substantially equal defect populations in the square root of each of the histograms.

7. The method of claim 1, wherein the one or more parameters of the detection algorithm used to separate the defects comprise actual detection value, wherein said separating comprises separating the defects into groups based on the regions and the defect type and separately determining for each group breakpoints defining the actual detection values corresponding to the bins for the different values, and wherein the defects having actual detection values below the lowest breakpoint are not separated into the bins.

8. The method of claim 1, wherein the defect type is defined based on polarity.

9. The method of claim 1, wherein the one or more parameters of the detection algorithm used to separate the defects comprise median value and actual detection value.

10. The method of claim 1, wherein distributing the user-specified target number proportionally across the bins for the different defect types comprises separately determining the number of the defects to be selected from each of the bins for the different defect types in each of the different regions by dividing a square root of number of defects of each of the different defect types in a region by the square root of the total number of defects in the region and multiplying results of said dividing by total number of defects to be selected from the region.

11. The method of claim 1, wherein distributing the user-specified target number across the bins for the different values for the one or more parameters comprises substantially evenly distributing the user-specified target number across the bins for the different values.

12. The method of claim 1, wherein said separating and said determining cause more of the defects in the defect sample to be selected from a transition area of a threshold curve than a non-transition area of the threshold curve.

13. The method of claim 1, wherein said selecting comprises randomly selecting the defects from the bins based on the determined numbers.

14. The method of claim 1, wherein the one or more parameters of the detection algorithm used to separate the defects comprise actual detection value, and wherein selecting the defects from the bins comprises selecting the defects from the bins in order from the bin corresponding to the highest actual detection value to the bin corresponding to the lowest actual detection value.

15. The method of claim 1, wherein said selecting comprises selecting only one defect from any cluster of defects included in any of the bins.

16. The method of claim 1, wherein the defect sample is created without any prior knowledge about the defect type or defect distribution across defect type.

17. The method of claim 1, wherein said selecting comprises selecting the defects from a first bin for the different values, and wherein if the number to be selected from the first bin cannot be selected from the first bin, said selecting further comprises substantially evenly redistributing the number of the defects that cannot be selected from the first bin across other bins for the different values in the same region and defect type as the first bin.

18. The method of claim 1, wherein at least a majority of the defects detected on the wafer are nuisance defects, and wherein at least a significant number of the defects in the defect sample are not nuisance defects.

19. The method of claim 1, wherein the inspection recipe comprises an inspection recipe for bright field inspection of the wafer.

20. The method of claim 1, wherein the inspection recipe comprises an inspection recipe for dark field inspection of the wafer.

21. The method of claim 1, wherein said separating comprises separating the defects into bins based on inspection system channel in which the defects were detected, the regions, the defect type, and the values of the defects for the one or more parameters of the detection algorithm.

22. The method of claim 21, wherein said determining comprises determining the number of the defects to be selected from each bin by further distributing the user-specified target number of defects across the bins for different inspection system channels in proportion to a number of the defects detected by each of the different inspection system channels.

23. The method of claim 1, wherein distributing the user-specified target number of defects across the bins for the different values for the one or more parameters is performed such that a ratio of the numbers of the defects to be selected from different bins for the different values is substantially the same as a ratio of the numbers of the defects in the different bins for the different values.

24. The method of claim 1, wherein the inspection recipe comprises an inspection recipe for dark field inspection of the wafer, and wherein said separating comprises separating the defects into groups based on inspection system channel in which the defects were detected, the regions, and the defect type and separately determining for each group breakpoints defining the values of the defects corresponding to the bins for the different values by generating a cumulated distribute function for each group and one of the one or more parameters, determining a square root of each of the cumulated distribute functions, and determining the breakpoints such that the bins for the different values of the one of the one or more parameters have substantially the same values of the cumulated distribute function.

25. A carrier medium, comprising program instructions executable on a computer system for performing a computer-implemented method for creating a defect sample for use in selecting one or more parameters of an inspection recipe, wherein the computer-implemented method comprises:
  separating defects into bins based on regions in which the defects are located, defect type, and values of the defects for one or more parameters of a detection algorithm, wherein the defects are detected on a wafer by performing a hot inspection on the wafer, and wherein the detection algorithm is included in an inspection recipe;
  determining a number of the defects to be selected from each bin by distributing a user-specified target number of defects across the bins for different regions and different defect types in proportion to a number of the defects in each of the different regions and having each of the different defect types and across the bins for different values for the one or more parameters, wherein distributing the user-specified target number proportionally across the bins for the different regions comprises separately determining the number of the defects to be selected from each of the bins for the different regions by dividing a square root of total number of defects in each of the different regions by the square root of the total number of defects detected on the wafer and multiplying results of said dividing by the user-specified target number; and
  selecting defects from the bins based on the determined numbers thereby creating a defect sample for use in selecting values of one or more parameters of the detection algorithm for use in the inspection recipe.

26. A system configured to create a defect sample for use in selecting one or more parameters of an inspection recipe, comprising:
  an inspection system configured to detect defects on a wafer by performing a hot inspection on the wafer; and
  a computer system configured to:
    separate the defects into bins based on regions in which the defects are located, defect type, and values of the defects for one or more parameters of a detection algorithm, wherein the detection algorithm is included in an inspection recipe;
    determine a number of the defects to be selected from each bin by distributing a user-specified target number of defects across the bins for different regions and different defect types in proportion to a number of the defects in each of the different regions and having each of the different defect types and across the bins for different values for the one or more parameters, wherein distributing the user-specified target number proportionally across the bins for the different regions comprises separately determining the number of the defects to be selected from each of the bins for the different regions by dividing a square root of total number of defects in each of the different regions by the square root of the total number of defects detected on the wafer and multiplying results of said dividing by the target number; and select defects from the bins based on the determined numbers thereby creating a defect sample for use in selecting values of one or more parameters of the detection algorithm for use in the inspection recipe.

* * * * *